United States Patent [19]

Carroll et al.

[11] Patent Number: 5,141,959
[45] Date of Patent: Aug. 25, 1992

[54] ISOPRENOID PHOSPHOLIPASE A2 INHIBITORS AND PREPARATIONS COMPRISING SAME

[75] Inventors: F. Ivy Carroll, Durham; Anita Lewin, Chapel Hill, both of N.C.; Kenneth Tramposch, East Amherst, N.Y.; Stephen A. Steiner, Bluffton, Ohio

[73] Assignee: Bristol-Myers Squibb Company, New York, N.Y.

[21] Appl. No.: 586,159

[22] Filed: Sep. 21, 1990

[51] Int. Cl.$^5$ ............... A61K 31/19; A61K 31/235; C07C 63/66; C07C 69/76
[52] U.S. Cl. ............... 514/568; 514/533; 562/488; 560/81
[58] Field of Search ............... 562/488; 560/81; 514/533, 568

[56] References Cited

U.S. PATENT DOCUMENTS

| | | | |
|---|---|---|---|
| 4,194,007 | 3/1980 | Van Scott et al. | 260/413 L X |
| 4,456,618 | 6/1986 | Dawson et al. | 560/56 X |
| 4,568,757 | 2/1986 | Carroll et al. | 562/488 X |

OTHER PUBLICATIONS

*Chemical Abstracts*, vol. 93, Oct. 13, 1980, No. 15, Columbus, Ohio, USA, p. 735, Abstract-No. 150 419c.
*Chemcial Abstracts*, vol. 95, No. 5, Aug. 3, 1981, Columbus, Ohio USA; p. 790; Abstract-No. 43 409u.

*Primary Examiner*—Jose G. Dees
*Assistant Examiner*—Vera C. Clarke
*Attorney, Agent, or Firm*—Oblon, Spivak, McClelland, Maier & Neustadt

[57] ABSTRACT

Compounds of the formula

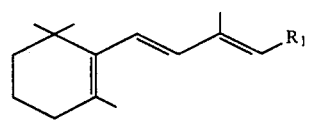
(A)

wherein $R_1$ is $CH=CY-C(CH_3)=CHX$ wherein X and Y are different and each is of the formula

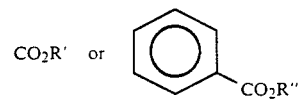

$CO_2R'$ or wherein R' and R" independently are H or alkyl of $C_{1-6}$ and $R_1$ includes all possible geometric isomers are demonstrated effective in treating inflammation, both topically and internally. The mechanism appears to be the inhibition of phospholipase $A_2$ enzymes.

11 Claims, 2 Drawing Sheets

ISOPRENOID PHOSPHOLIPASE A2 INHIBITORS AND PREPARATIONS COMPRISING SAME

BACKGROUND OF THE INVENTION

1. Field of the Invention

This invention pertains to retinoid derivatives showing phospholipase $A_2$ ($PLA_2$) inhibitory activity, and pharmaceutical preparations comprising these compounds. Similarly, a method of inhibiting $PLA_2$, in mammals, is addressed.

2. Background of the Prior Art

Phospholipases are enzymes which catalyze the hydrolysis of membrane phospholipids releasing free fatty acids. In mammalian tissues, phospholipase $A_2$ ($PLA_2$) is a calcium-dependent enzyme which specifically cleaves the sn-2-acyl bond of phospholipids to yield free arachidonic acid and a lysophospholipid. [*Van den Bosch H. Biochem Biophys Acta*, 604,191–246 (1980)]. Both products of this reaction can serve as starting points for the biosynthesis of inflammatory mediators. Arachidonic acid can be converted by the cyclooxygenase and lipoxygenase pathways to the proinflammatory prostaglandins and leukotrienes. [*Higgs GA and Vane JR, Br Med Bull*, 39, 265 (1983)]. Lysophospholipids can be utilized by certain cell types to produce platelet-activating-factor (PAF), a potent inflammatory mediator. [*Chilton FH et al, J. Biol Chem*, 257, 5402 (1982)].

Many non-steroidal anti-inflammatory agents, such as indomethacin, inhibit the cyclooxygenase reaction and therefore block the formation of prostaglandins from arachidonic acid. A number of compounds also have been discovered which are lipoxygenase inhibitors. [*Gordon Jones et al, J. Med Chem*, 29, 1504–1511 (1986)]. [*Mardin M and Busse WD, In: Leukotrienes and other Lipoxygenase Products*, (Ed) P. J. Piper, Prostaglandin Series, pp. 3, 263–274, Chichester Research Studies Press]. These compounds block the formation of leukotrienes and have also been shown to have anti-inflammatory effects. In addition, several compounds have been reported to be dual lipoxygenase/cyclooxygenase inhibitors [*Salmon J A, Simmons P M and Moncada S H, J Phar Pharmac* 35, 808 (1983)]. [*Bonney R J et al, Biochem Pharmacol*, 36, 22, 2885–2891 (1987)]. It is thought that these compounds, by virtue of their more complete blockade of the arachidonic acid cascade, would be more effective anti-inflammatory agents. An inhibitor of phospholipase $A_2$ would be expected to reduce the production of the same mediators as would a dual lipoxygenase/cyclooxygenase inhibitor. However, this reduction would be achieved via inhibition of arachidonic acid release. In addition, inhibition $PLA_2$ would result in a reduction of PAF production. As a result, inhibition of $PLA_2$ activity represents an attractive approach for the development of novel agents for the treatment of inflammatory disorders.

A wide variety of retinoids, and related retinoic acid derivatives, are known in the art. Thus, U.S. Pat. No. 4,568,757, Carroll et al, discloses configurationally locked retinoids. U.S. Pat. Nos. 4,126,693 and 4,055,659, Gander et al, as well as U.S. Pat. No. 4,194,007 describe various retinoids which are generally esters and amides of trans-retinoic acid as well as derivatives thereof. These patents generally ascribe "vitamin A-type activity" to the various retinoids described therein, and specifically describe the use of these compounds in the treatment of skin diseases or abnormal states, abnormal keratinization, acne, etc., as well as their use as sunscreen agents.

Additional art references are available describing the preparations of various retinoids and retinoid intermediates. U.S. Pat. No. 2,662,914, describes a retinoic acid derivative with a carboxylic acid substituent at the 14 position, while Lewin et al, [*Journal of Organic Chemistry*, 48, 222 (1983) and *Journal of American Chemical Society*, 103, 2527 (1981)] describe the synthesis of various retinoids. Other retinoids, and $PLA_2$ inhibitors are addressed in C. Fiedler [*Nagy et al, Agents and Actions*, 46, 620–621 (1985) and 27, 313–315 (1989)]; *A. A. Fawzy et al, [Agents and Actions*, 25, 394–400 (1988)]; *A. C. Hanglow et al, [Agents and Actions*, 27, 347–350 (1989)] and *C. Marcelo et al, [Clin. Res.*, 34, 766A (1986)].

It is the object of this invention, therefore, to provide retinoid compounds which have $PLA_2$ inhibitor properties, and compositions including those compounds which are useful in the treatment of inflammatory diseases, such as arthritis, inflammatory bowel disorder and numerous related conditions characterized by manifest inflammation.

SUMMARY OF THE INVENTION

The invention resides in the discovery that a compound of the structural formula A

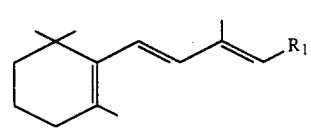

(A)

wherein $R_1$ is CH=CY—C(CH$_3$)50 CHX wherein X and Y are different and each is of the formula

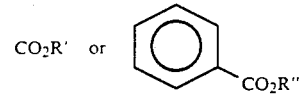

wherein R' and R" are independently H or alkyl of $C_{1-6}$ and $R_1$ includes all possible geometric isomers exhibits pronounced $PLA_2$ activity inhibition, and demonstrates marked anti-inflammatory effects.

This family of structural isomers, and their pharmaceutically acceptable salts, may be combined with pharmaceutically acceptable carriers in the form of a lotion, cream or gel for topical application or alternatively, if desired, compounded into tablet form or as an elixir for internal application.

DETAILED DESCRIPTION OF THE INVENTION

Figure 1:
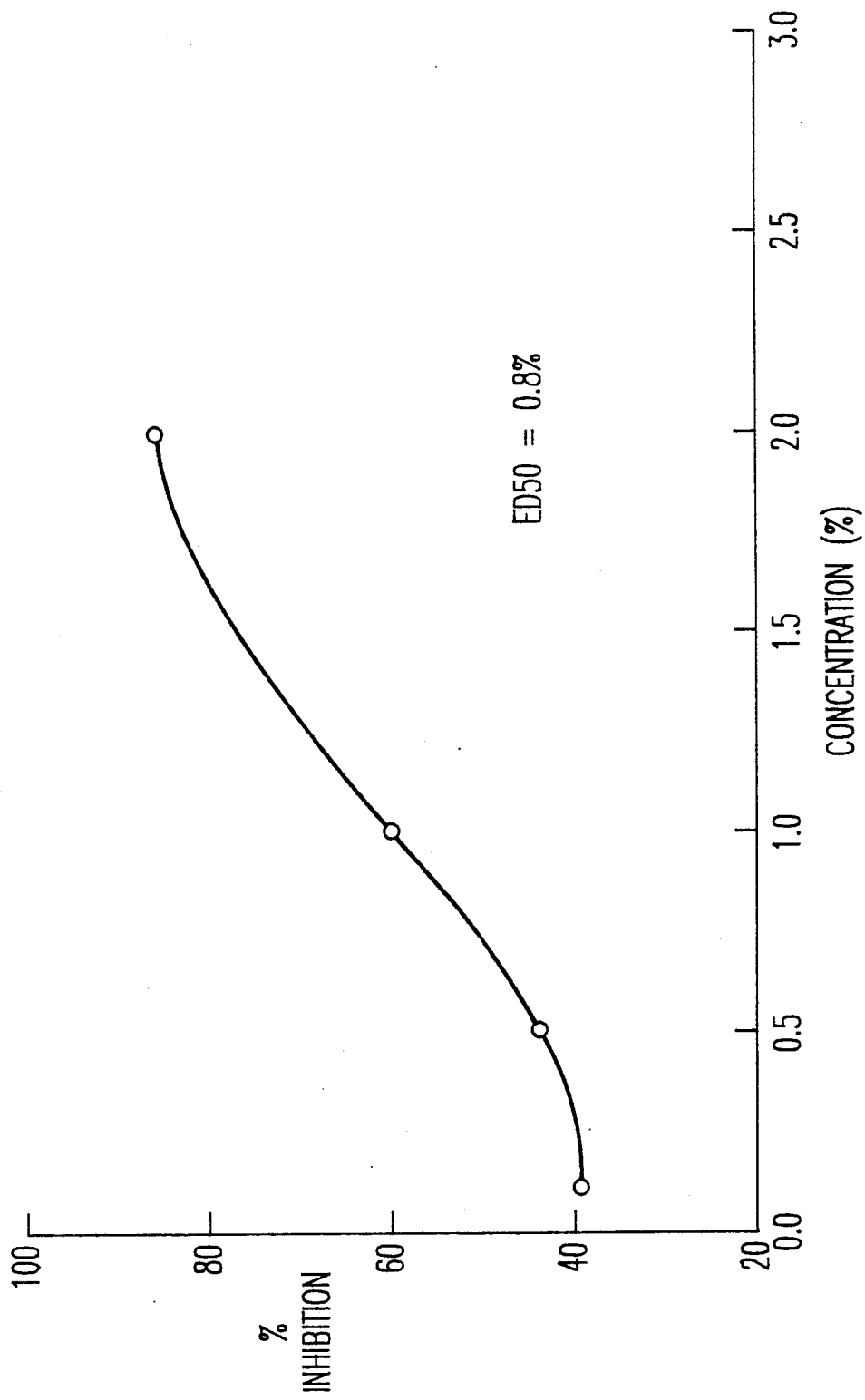
FIG. 1 is a graph showing the anti-inflammation effect of the invention, as a function of dosage concentration graphed against ear weight increase.

The family of structural isomers of the invention includes eight distinct compounds, set forth in Table 1 below:

TABLE 1

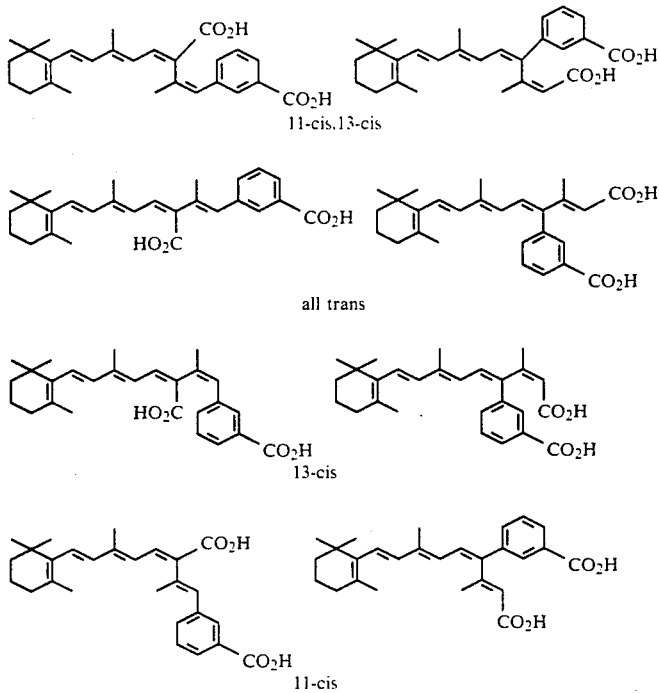

In the practice of this invention, these isomers may be used in substantially purified form, or as mixtures of a plurality of isomers. It is to be expected that activity will vary, from application to application, and isomeric form to isomeric form. However, all of the isomers appear active, having the anti-inflammatory characteristics of interest herein, and so may be used singly or in combination.

The compounds of the invention may be made pursuant to prior art synthesis practices, including those set forth in U.S. Pat. No. 4,568,757, the entire content of which is incorporated herein, by reference. Other synthesis schemes will occur to those of ordinary skill in the art, and do not, per se, constitute an aspect of this invention. An exemplary synthesis route is included.

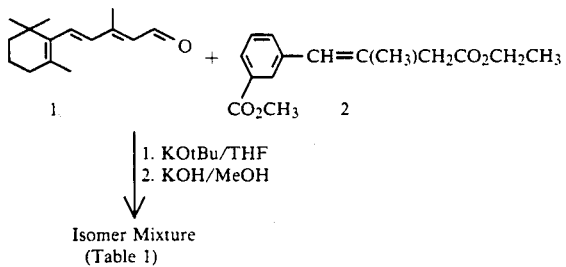

PREPARATION OF ISOMER MIXTURE

The following reaction and subsequent manipulations, unless otherwise noted, were carried out in a room equipped with dim red lights. Potassium tert-butoxide (7.80 g, 0.069 mol) was placed in an oven-dried 3-necked 1000 ml round-bottomed flask under $N_2$. Anhydrous tetrahydrofuran (350 ml) was added and the mixture cooled to 0° C. for 10 min. A solution of 2 (11.7 g, 0.045 mol) in 200 ml of anhydrous tetrahydrofuran was added dropwise. The resulting red solution was stirred at 0° C. for 15 min. A solution of 1 (9.74 g, 0.045 mol) in 200 ml of anhydrous tetrahydrofuran was added dropwise. This very dark solution was stirred at 0° C. for 1.5 h, then the tetrahydrofuran was removed via rotary evaporation at 30° C. The residue was dissolved in 350 ml of 3M potassium hydroxide/methanol, and resulting solution heated to reflux for 2 h. The solution was allowed to cool to room temperature then was diluted with water and extracted with diethyl ether. The aqueous layer was acidified with 3N HCl and extracted with diethyl ether. The organic layer was separated from the aqueous layer and dried over $Na_2SO_4$. Filtration and removal of solvent by rotary evaporation afforded the isomer mixture as 14.5 g of a foamy solid.

PREPARATION OF 13-CIS-12-(3'-CARBOXYPHENYL)RETINOIC ACID (COMPOUND I)

The solid was purified by preparative HPLC (Waters PrepPak 500 C-18 column; 37.5% $CH_3CN$:62.5% 1% $NH_4OAc$). The appropriate fractions (checked by analytical HPLC) were rotary evaporated to remove the $CH_3CN$, and the resulting aqueous solution was acidified with conc. HCl and extracted with diethyl ether. Filtration and rotary evaporation of the ether afforded 3.21 g of slightly impure product. Recrystallization from ethyl acetate/hexane furnished 2.0 g of pure product, mp 117°–118° C. $^1H$ NMR (250 MHz, dioxane-$d_8$) δ(ppm) 7.93–7.90 (m, 2H, 1', 6'—ArH), 7.54–7.50 (m, 2H, 4', 5'—Ar—H), 6.63 (d, J=12 Hz, 1 H, H-11), 6.19 (d, J=16 Hz, 1H, H-7), 6.10 (d, J=12 Hz, 1 H, H-10), 5.91 (d, J=16 Hz, 1H, H-8), 5.85 (app s, 1 H, H-14), 1.96 (s, 3 H, 9a or 13a—$CH_3$), 1.90 (s, 3H, 9a or 13a-$CH_3$), 1.63 (s, 3H, 5a—$CH_3$), 1.60–1.19 (m, 6 H, H-2–4), 0.99 (s, 6H, 2(1a)—$CH_3$).

The compounds of the invention may be prepared in a form suitable for topical administration, particularly as a cream or gel, for treatment of localized inflammation including an opthalmic preparation, such as eye drops or the like, for treatment of inflammation of ocular tissues. Alternatively, the compounds, particularly compounded into tablet form, or mixed with a diluent and carrier, as well as potentially other active agents, in an elixir, for internal application, is envisioned. Further, the compounds of the invention may be incorporated in delayed release formulations, such as biodegradable polymer matrices, which release the compound over time, at a sustained level, upon implantation of the delayed release material. Examples of delayed release polymers include polymers based on polycaprolactones, lactides, glycols and the like.

Concentrations in effective dosage ranges will vary from compound to compound, patient to patient, and syndrome or disease state treated. Generally, for topical applications, an anti-inflammatory amount of the compounds will range from 0.005% to 10% w/v in a suitable topical dosage form. Dosage values for internal application should be confined to a range of 0.1 mg/kg to 50 mg/kg per day. When compounded in the form of a continuous release device, or a sustained delivery device, concentration values will be altered depending on the nature of the polymer matrix or reservoir-defining material employed. In general, sustained delivery devices should be prepared so as to deliver a constant dosage within the above value. Migration and diffusion rates can be established, for a given polymer, according to art recognized practices, that do not constitute an aspect of the invention.

This invention and its effectiveness can be further understood by reference to the following in vitro and in vivo experiments.

EXAMPLES

PLA$_2$ Inhibition Assay

This assay is used to measure the inhibition of human platelet PLA$_2$ by test compounds. The method used was similar to that reported by Franson et al. [*Jesse RL and Franson RC, Biochem Biophys Acta*, 575, 467–470 (1979)]. [*Franson RC, Patriarca P and Elsback P, J Lipid Res* 15, 380–388 (1974)]. The enzyme was isolated from human platelets. The substrate used consisted of $^{14}$C-oleate labeled E. coli membranes. E. Coli cells were grown in the presence of $^{14}$C-oleic acid and then autoclaved to prepare membranes. In the assay, various concentrations of test compounds are preincubated with PLA$_2$ (7.5 μg/ml) in a buffer consisting of 25 mM HEPES (pH 7) 150 mM NaCl, 5.0 mM Cacl$_2$, and 10% DMSO (test compound solvent) at 37° C. for 7 minutes. The E. coli membrane substrate is then added (0.1 mM phospholipid, 0.5 μCi/umol) and the reaction is incubated at 37° C. for 30 minutes. The final reaction volume is 0.1 ml. The reaction is quenched with tetrahydrofuran (1.9 ml), and the entire solution is applied to a solid-phase extraction column (aminopropyl resin, Analytichem). The column is rinsed with an additional 1 ml of tetrahydrofuran. The free fatty acid is eluted from the column with 1.0 ml of 2% acetic acid in tetrahydrofuran and collected in a scintillation vial. The amount of free fatty acid product is determined by liquid scintillation counting. The amount of inhibition produced by the test compound is calculated by comparing the number of counts obtained in the presence of the compound to that obtained for the control reactions (test compound solvent only). Percent inhibition values are determined by the equation:

$$\% \text{ Inhibition} = \left( \left| \frac{\text{(cpm in sample)} - \text{(background)}}{\text{(cpm in control)} - \text{(background)}} \right| \right) \times 100$$

IC$_{50}$ values (the concentration of inhibitor required to produce 50% inhibition) are determined by interpolation of a plot of % inhibition versus log concentration.

The results in Table 2 report IC$_{50}$ values for inhibition of human platelet PLA$_2$ by selected compounds. The data demonstrate that these compounds dose-dependently inhibit phospholipase A$_2$.

TABLE 2

| Inhibition of Human Platelet Phospholipase A$_2$ | |
|---|---|
| Compound I | IC$_{50}$ |
| Compound | 40 |
| Isomer | 39 |
| Comparison (structure with CO$_2$H) | >500 |

PHORBOL ESTER-INDUCED SKIN INFLAMMATION ASSAY

Anti-inflammatory activity of the test compounds was determined in the phorbol ester-induced mouse ear inflammation model. [*Young J M, Wagner B M and Spires D A, J Invest Dermatol*, 80, 48–52 (1983)]. In this assay, an inflammatory reaction is induced by the topical application of 0.01% (w/v) tetradecanoylphorbol-13-acetate (TPA) to the ears of CD-1 mice. An acute inflammatory reaction results in which the ears swell and inflammatory cells infiltrate the ear tissue. TPA, with and without various concentrations of test compound, was applied to the inner and outer aspects of the ears (10 μl/surface). After six hours, the mice were sacrificed and the ears were removed. Ear tissue punches (5/16") were taken from each ear and weighed to measure edema. The ear punches were then processed for the determination of neutrophil accumulation by measurement of myeloperoxidase (MPO) activity by the method of Bradley et al. [*Bradley P P et al, J Invest Dermatol*, 78, 206–209 (1982)]. MPO is a specific marker for the presence of neutrophils in tissue.

The anti-inflammatory activity produced by the test compound is calculated by comparing the edema or MPO values obtained for the drug-treated ears to those obtained for non-drug treated ears. Percent inhibition values were determined by the equation:

$$\% \text{ Inhibition} = \left( \left| \frac{(TP1 + \text{drug-treated group}) - (\text{untreated control group})}{(TP1 - \text{only treated group}) - (\text{untreated control group})} \right| \right) \times 100$$

Figure 2:
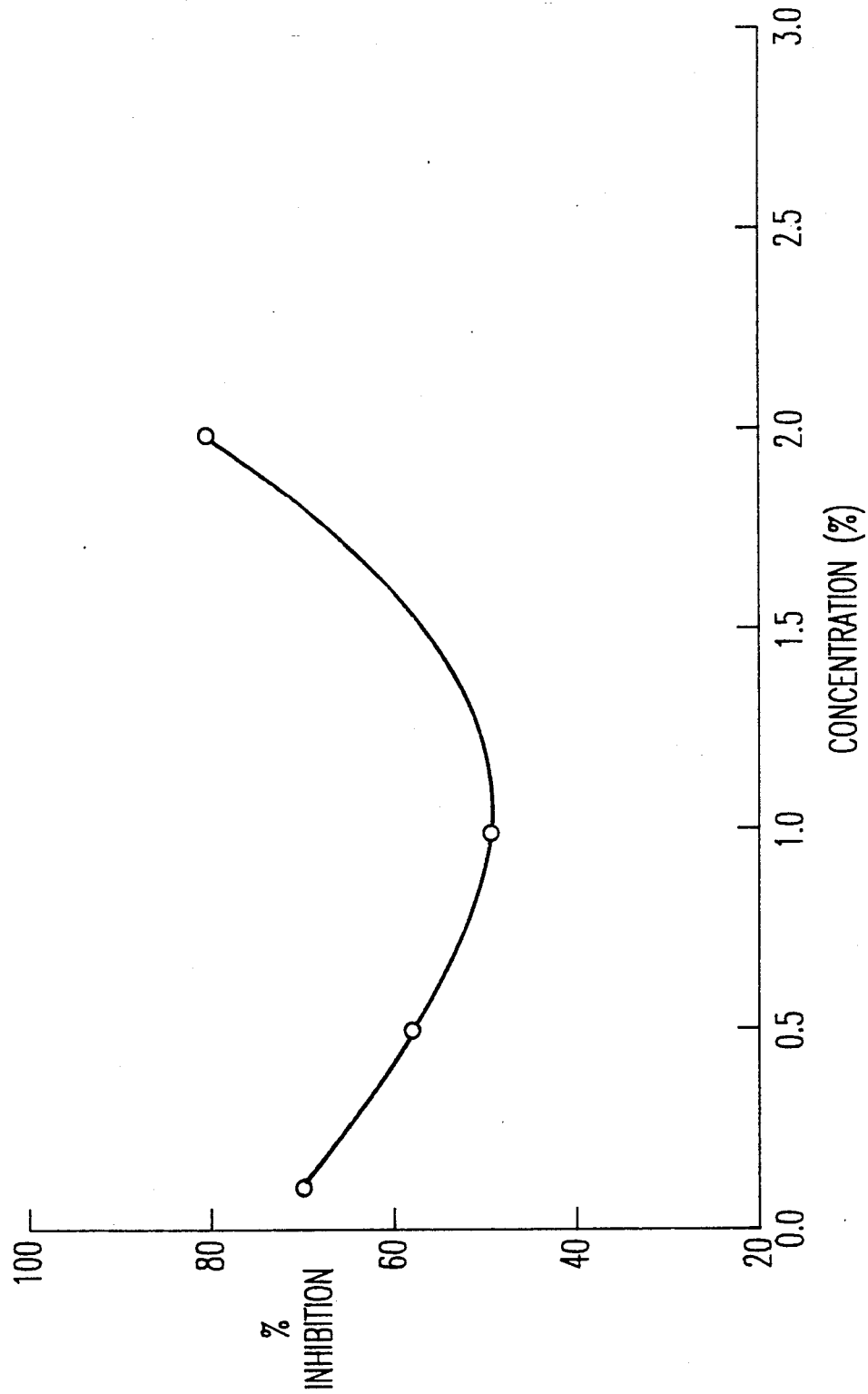
FIG. 2 is a graph demonstrating the effect of the claimed invention on myeloperoxidase activity, as a function of percent concentration.

The data for compound I is shown in FIG. 1. Compound I dose-dependently blocks TPA-induced mouse ear edema. The ED$_{50}$ is estimated to be 0.8%. The dose response data for inhibition of cell infiltration is shown in FIG. 2. The ED$_{50}$ for this parameter was found to be <0.1%. This compound effectively blocks edema and cell infiltration in this model.

The invention of this application has been described with reference to specific embodiments, and generic description. Variations on the embodiments disclosed therein will occur to those of ordinary skill in the art without the exercise of inventive faculty. Such variations, including, in particular, the addition of other active agents, the use of additional carriers, diluents, adjuvants and the like, as well as variation in period of administration balanced against dosage value, are embraced within the invention, save for the limitations positively recited in the claims set forth below.

What is claimed is:

1. A compound of the formula A

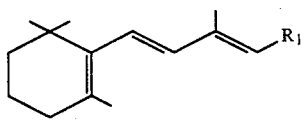 (A)

wherein $R_1$ is $CH=CY—C(CH_3)=CHX$ wherein X and Y are different and each is of the formula

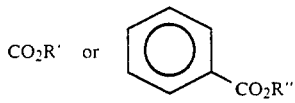

wherein R' and R" independently are H or alkyl of $C_{1-6}$ and $R_1$ includes all possible geometric isomers.

2. The compound of claim 1, selected from the group consisting of

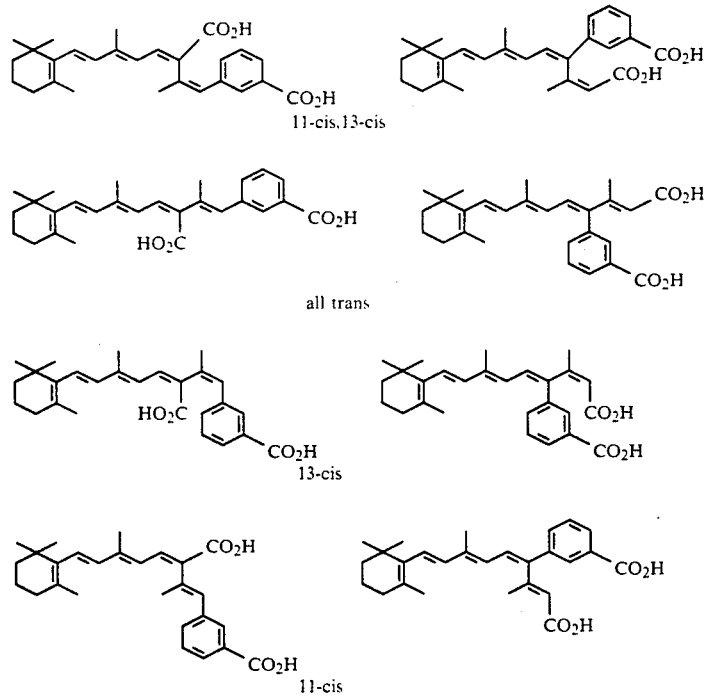

and mixtures thereof.

3. A method of treating inflammation of skin or membranes of a mammal, comprising periodically topically applying a pharmaceutically effective amount of the compound of claim 1, to said inflamed area, until said inflammation subsides.

4. A method of treating inflammation of skin or membranes of a mammal, comprising periodically topically applying a pharmaceutically effective amount of the compound of claim 2, to said inflamed area, until said inflammation subsides.

5. The method of claim 3, wherein said compound is incorporated in a pharmaceutically acceptable carrier, in the form of a lotion, cream or gel.

6. A method of treating an inflammatory disorder in a mammal, comprising administering a pharmaceutically effective amount of the compound of claim 1 to said mammal until the inflammation disorder subsides.

7. The method of claim 6, wherein said pharmaceutically effective amount is between 0.1 mg/kg to 50 mg/kg.

8. A topical pharmaceutical preparation effective in reducing inflammation of surface tissues in a mammal, comprising an inflammation-reducing effective amount of the compound of claim 1, in a carrier acceptable for topical pharmaceutical application.

9. The topical pharmaceutical preparation of claim 8, wherein said amount is 0.005% to 10%.

10. The topical pharmaceutical preparation of claim 8, wherein said preparation is an opthalmic one, said carrier being acceptable for application to ocular tissues.

11. A pharmaceutical preparation effective for treating inflammation in a mammal, comprising a pharmaceutically effective amount of the compound of claim 1, admixed with a pharmaceutically acceptable carrier.